United States Patent [19]

Ranken

[11] Patent Number: 4,532,326
[45] Date of Patent: Jul. 30, 1985

[54] DECARBOXYLATION PROCESS FOR PREPARING 4-(3-AMINOPHENYL)PYRIDINES

[75] Inventor: Paul F. Ranken, Baton Rouge, La.

[73] Assignee: Ethyl Corporation, Richmond, Va.

[21] Appl. No.: 537,085

[22] Filed: Sep. 29, 1983

[51] Int. Cl.$^3$ .................. C07D 215/16; C07D 213/24
[52] U.S. Cl. .................................... 546/156; 546/329; 546/335; 544/94
[58] Field of Search ................. 544/94; 546/156, 329, 546/335

[56] References Cited

U.S. PATENT DOCUMENTS

| | | | |
|---|---|---|---|
| 3,753,993 | 8/1973 | Lesher | 260/286 R |
| 3,907,808 | 9/1975 | Lesher | 260/287 R |
| 4,118,557 | 10/1978 | Lesher | 542/420 |

OTHER PUBLICATIONS

Mitscher et al, J. Med. Chem., 1978, vol. 21, pp. 485–489.
Morrison et al, Organic Chem., pp. 446–447.

Primary Examiner—Donald G. Daus
Assistant Examiner—Cecilia Shen
Attorney, Agent, or Firm—Donald L. Johnson; John F. Sieberth; Patricia J. Hogan

[57] ABSTRACT

4-(3-Aminophenyl)pyridines, useful in the preparation of 1-alkyl-1,4-dihydro-4-oxo-7-pyridinyl-3-quinolinecarboxylic acids, are prepared by heating a 2-amino-4-(4-pyridinyl)benzoic acid at decarboxylation temperatures.

5 Claims, No Drawings

DECARBOXYLATION PROCESS FOR PREPARING 4-(3-AMINOPHENYL)PYRIDINES

FIELD OF THE INVENTION

This invention relates to 4-(3-aminophenyl)pyridines and more particularly to a process for preparing them.

BACKGROUND

As disclosed in Sterling Drug's U.S. Pat. Nos. 3,753,993 (Lesher et al.), 3,907,808 (Lesher and Carabateas), and 4,118,557 (Lesher) and in copending applications Ser. No. 495,977 (Walter I), filed May 19, 1983; Ser. No. 497,026 (Ramachandran I) and Ser. No. 497,027 (Ramachandran II), both filed May 23, 1983; Ser. No. 511,831 (Ramachandran and Ranken), Ser. No. 511,832 (Ramachandran, Ranken, and Wiegand), and Ser. No. 511,913 (Ranken and Ramachandran), all filed July 8, 1963, it is known that antibacterial 1-alkyl-1,4-dihydro-4-oxo-7-pyridinyl-3-quinolinecarboxylic acids can be prepared from 4-(3-aminophenyl)pyridines.

From Mitscher et al., "Quinoline Antimicrobial Agents. 1. Versatile New Synthesis of 1-Alkyl-1,3-dihydro-4-oxo-3-quinolinecarboxylic Acids," *Journal of Medicinal Chemistry*, 1978, Vol. 21, No. 5, pp. 485-489, it is also known that antimicrobial agents related to the aforementioned bactericides can be prepared from the appropriate isatoic anhydrides. Copending applications Ser. No. 511,844 (Ranken and Walter), Ser. No. 511,854 (Ramachandran III), and Ser. No. 511,887 (Walter II), all filed July 8, 1983, and Ser. No. 523,462 (Walter and Ranken), filed Aug. 15, 1983, show that those bactericides can be prepared by a route similar to that employed by Mitscher et al.—a route utilizing a 2-amino-4-(4-pyridinyl)-benzoic acid as an intermediate.

Since each of the aforementioned processes for preparing 1-alkyl-1,4-dihydro-4-oxo-7-pyridinyl-3-quinolinecarboxylic acid bactericides is a complicated process involving the preparation of several intermediates, it is sometimes desirable to have different stages of the processes performed by different manufacturers. Versatility could thus be contributed by making it possible to cross over from one process to the other, i.e., convert an intermediate useful for preparing the bactericides by one technique to an intermediate suitable for preparing the bactericides by another technique. It would also be desirable to find an alternative technique of preparing 4-(3-aminophenyl)pyridines.

SUMMARY OF INVENTION

An object of this invention is to provide a novel process for preparing 4-(3-aminophenyl)pyridines.

Another object is to provide a process for preparing 4-(3-aminophenyl)pyridines from 2-amino-4-(4-pyridinyl)benzoic acids.

A further object is to provide novel processes for preparing 1-alkyl-1,4-dihydro-4-oxo-7-pyridinyl-3-quinolinecarboxylic acids from 2-amino-4-(4-pyridinyl)-benzoic acids.

These and other objects are attained by heating a 2-amino-4-(4-pyridinyl)benzoic acid at a decarboxylation temperature to form a 4-(3-aminophenyl)pyridine and, when desired, converting the 4-(3-aminophenyl)-pyridine to a derivative thereof.

DETAILED DESCRIPTION

2-Amino-4-(4-pyridinyl)benzoic acid useful in the practice of the invention are compounds corresponding to the formula:

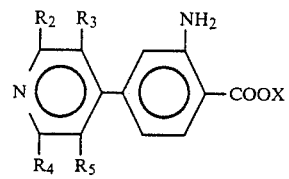

wherein X is hydrogen or an alkali metal and $R_2$, $R_3$, $R_4$, and $R_5$ are independently selected from hydrogen and innocuous substituents, such as substituted (e.g., halogenated) and unsubstituted aryl or aryloxyaryl groups, halo, etc.—the preferred acids being 2-amino-4-(4-pyridinyl)benzoic acid and its alkali metal salts. These compounds are preferably prepared by the processes of Ranken and Walter or the processes of Ramachandran III, the teachings of both of which are incorporated herein by reference. Thus, they may be prepared, e.g., by oxidizing a 4-(4-alkyl-3-nitrophenyl)pyridine to a 2-nitro-4-(4-pyridinyl)benzoic acid and reducing the nitro group to an amino group or by treating a 4-(4-alkyl-3-nitrophenyl)pyridine with an alcoholic base.

The decarboxylation is accomplished simply by heating the acid at a decarboxylation temperature, e.g., at a temperature in the range of about 200°-300° C., preferably about 240°-250° C., for a time sufficient to effect the decarboxylation. This time can vary from a few minutes to a few hours, depending on the particular decarboxylation temperature employed.

The process results in the formation of the 4-(3-aminophenyl)pyridine corresponding to the acid used as a starting material, i.e., a compound corresponding to the formula:

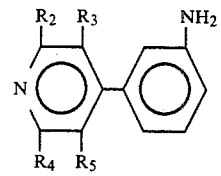

wherein $R_2$, $R_3$, $R_4$, and $R_5$ have the same definitions as given above.

As indicated above, the 4-(3-aminophenyl)pyridines produced by the decarboxylation process can be used in the production of antibacterial agents, such as the 1-alkyl-1,4-dihydro-4-oxo-7-pyridinyl-3-quinolinecarboxylic acids of Lesher, Lesher et al., and Lesher and Carabateas. When these bactericides or their intermediates are desired, they may be prepared by subjecting the 4-(3-aminophenyl)pyridines to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to a 1-alkyl-1,4-dihydro-4-oxo-7-(4- pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to receive a desired product for use in any other desired process, etc.

The following example is given to illustrate the invention and is not intended as a limitation thereof.

EXAMPLE

A sample of 2-amino-4-(4-pyridinyl)benzoic acid was heated at 240°–245° C. for four hours. HPLC analysis of the product showed 9 area % 2-amino-4-(pyridinyl)benzoic acid, 7 area % unknown, and 84 area % 4-(3-aminophenyl)pyridine.

It is obvious that many variations may be made in the products and processes set forth above without departing from the spirit and scope of the invention.

I claim:

1. A process which comprises heating a 2-amino-4-(4-pyridinyl)benzoic acid at a decarboxylation temperature in the range of about 200°–300° C. to prepare a 4-(3-aminophenyl)pyridine.

2. The process of claim 1 wherein the 2-amino-4-(4-pyridinyl)benzoic acid is 2-amino-4-(4-pyridinyl)benzoic acid.

3. The process of claim 1 wherein the decarboxylation temperature is a temperature in the range of about 240°–250° C.

4. In a process for preparing a 1-alkyl-1,4-dihydro-4-oxo-7-(4-pyridyl)-3-quinolinecarboxylic acid by (a) reacting a 4-(3-aminophenyl)pyridine with a dialkyl ethoxymethylenemalonate, (b) cyclizing the resultant dialkyl 3-(4-pyridyl)anilinomethylenemalonate, (c) N-alkylating the resultant alkyl 1,4-dihydro-4-oxo-7-(4-pyridyl)-3-quinolinecarboxylate, and (d) hydrolyzing the resultant alkyl 1-alkyl-1,4-dihydro-4-oxo-7-(4-pyridyl)-3-quinolinecarboxylate, the improvement which comprises preparing the 4-(3-aminophenyl)pyridine by heating a 2-amino-4-(4-pyridinyl)benzoic acid at a decarboxylation temperature in the range of about 200°–300° C.

5. In a process for preparing a 1-alkyl-1,4-dihydro-4-oxo-7-(4-pyridyl)-3-quinolinecarboxylic acid by (a) converting a 4-(3-aminophenyl)pyridine to a 3-(4-pyridyl)-N-alkylaniline, (b) reacting the 3-(4-pyridyl)-N-alkylaniline with a dialkyl ethoxymethylenemalonate, (c) cyclizing the resultant dialkyl 3-(4-pyridyl)-N-alkylanilinomethylenemalonate, and (d) hydrolyzing the resultant alkyl 1-alkyl-1,4-dihydro-4-oxo-7-(4-pyridyl)-3-quinolinecarboxylate, the improvement which comprises preparing the 4-(3-aminophenyl)pyridine by heating a 2-amino-4-(4-pyridinyl)benzoic acid at a decarboxylation temperature in the range of about 200°–300° C.

* * * * *